(12) United States Patent
Siilats

(10) Patent No.: US 9,002,067 B2
(45) Date of Patent: Apr. 7, 2015

(54) SYSTEMS AND METHODS FOR DETECTING BLOOD ALCOHOL LEVEL

(71) Applicant: Keith Siilats, New York, NY (US)

(72) Inventor: Keith Siilats, New York, NY (US)

(73) Assignee: Bytelogics Inc., New York, NY (US)

( * ) Notice: Subject to any disclaimer, the term of this patent is extended or adjusted under 35 U.S.C. 154(b) by 195 days.

(21) Appl. No.: 13/852,070

(22) Filed: Mar. 28, 2013

(65) Prior Publication Data
US 2014/0294245 A1     Oct. 2, 2014

(51) Int. Cl.
*G06F 9/00*     (2006.01)
*A61B 3/113*     (2006.01)
*G06T 7/20*     (2006.01)

(52) U.S. Cl.
CPC ....... *A61B 3/113* (2013.01); *G06T 2207/10016* (2013.01); *G06T 2207/30041* (2013.01); *G06T 7/20* (2013.01); *G06T 7/2033* (2013.01)

(58) Field of Classification Search
None
See application file for complete search history.

(56) References Cited

U.S. PATENT DOCUMENTS

| | | | | |
|---|---|---|---|---|
| 5,422,690 | A * | 6/1995 | Rothberg et al. | 351/209 |
| 8,317,328 | B1 * | 11/2012 | Harris et al. | 351/210 |
| 8,899,748 | B1 * | 12/2014 | Migdal | 351/206 |
| 2004/0233061 | A1 * | 11/2004 | Johns | 340/575 |
| 2007/0132950 | A1 * | 6/2007 | Victor et al. | 351/200 |
| 2008/0151064 | A1 * | 6/2008 | Saito et al. | 348/208.4 |
| 2010/0280372 | A1 * | 11/2010 | Poolman et al. | 600/437 |
| 2015/0025917 | A1 * | 1/2015 | Stempora | 705/4 |

OTHER PUBLICATIONS

Karl Citek, O. D., O. D. Bret Ball, and A. Rutledge Dale. "Nystagmus testing in intoxicated individuals."*

* cited by examiner

*Primary Examiner* — Aaron W Carter
*Assistant Examiner* — Narek Zohrabyan
(74) *Attorney, Agent, or Firm* — Patent Jurist; Georgiy L. Khayet

(57) ABSTRACT

Provided are systems and methods for detecting blood alcohol level. The system for detecting blood alcohol level comprises a receiver configurable to receive an input video of an eye of a user and a processor configurable to: stabilize the input video; analyze the input video; based on the analysis, detect a horizontal gaze nystagmus level; and based on the horizontal gaze nystagmus level, determine an equivalent blood alcohol level of the user. The system outputs data associated with the equivalent blood alcohol level via an interface. Additionally, the system comprises a screen configurable to display a moving object. The input video captures eye movements of the user following the moving object. To illuminate the eye of the user, the system may generate red light.

20 Claims, 10 Drawing Sheets

SYSTEMS AND METHODS FOR DETECTING BLOOD ALCOHOL LEVEL

FIELD

This application relates generally to systems and methods for detecting involuntary eye movements of a user and, more specifically, systems and methods for detecting a blood alcohol level based on involuntary eye movements.

BACKGROUND

An involuntary jerking or bouncing of an eyeball may be noticed under the influence of alcohol or certain other central nervous system depressants. Such involuntary movements, called nystagmus, may be a result of alcohol caused hindering of the ability of the brain to correctly control eye muscles. Horizontal gaze nystagmus (HGN) refers to a lateral or horizontal jerking when the eye gazes to the side. With an increase of blood alcohol level, the degree of hindering becomes greater; thus the jerking becomes more noticeable. The degree of HGN may be assessed to detect blood alcohol level.

Conventional horizontal and/or vertical gaze nystagmus tests are part of field sobriety tests used by law enforcers and medics to assess alcohol impairment of a person. However, accuracy and reliability of conventional HGN tests are subject to challenge. Device-assisted tests may be influenced by hand and/or head shaking and other factors.

Moreover, conventional methods are intended for policemen and medics, rather than users willing to assess own blood alcohol level.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are systems and methods for detecting a blood alcohol level based on involuntary eye movements, specifically horizontal gaze nystagmus. The method for detecting a blood alcohol level may comprise displaying a moving object on a screen of a user device. The moving object may move from one side of the screen to the opposite side one or more times. The user may follow the moving object with his eyes. An eye of the user may be captured while following the moving object; thus an input video may be received. The input video may be captured in a red light provided by a light source or the screen.

Then, the input video may be stabilized to compensate for movements of the head of the user and/or a hand that holds the user device. However, the eye movements may interfere with the stabilization. To avoid this, an eye area may be detected in the input area, and a mask may be created to mask the detected eye area in all frames of the input video. Thus, an eye area may become a masked portion and the rest of each frame may become an unmasked portion. Based on the unmasked portion, the input video may be stabilized, and a shaking movement of the receiver may be detected.

The detected shaking movement may be applied to the masked portion to eliminate the shaking of the video. Then, the mask may be analyzed to identify a pupil of the user in the mask. Based on the analysis, a horizontal gaze nystagmus level may be determined. In some embodiments, detecting of the horizontal gaze nystagmus level may include estimating a velocity of the pupil between the plurality of frames in the input video, and based on the estimation, determining a shift in the velocity. The determined shift may be used to determine the horizontal gaze nystagmus level corresponding to the shift in a lookout table.

According to the horizontal gaze nystagmus level, an equivalent blood alcohol level of the user may be determined, and the data associated with the equivalent blood alcohol level may be output on the screen of the user device.

In some embodiments, the shaking movement and eye movement can be detected together with the use of compressed sensing algorithms, such as Robust Principal Component Analysis (RPCA). The algorithm can separate the video into a low rank component that captures the change in lighting or camera shake, and a sparse component that captures the pixels of a moving eyeball.

In some embodiments, to get more accurate individual test results, the user may perform one or more calibration tests. A calibration test may include determining a blood alcohol level of the user using the described method and inputting an actual alcohol level. In various embodiments, the actual alcohol level may be either measured by an alcohol measure unit or estimated by the number of drinks in the last hour. A series of calibration tests may be performed with different alcohol levels of the user. Then, the determining of the equivalent blood alcohol level may be adjusted based on the calibration tests associated with the user.

Additionally, in some embodiments, safety recommendations may be provided based on the output equivalent alcohol level. The safety recommendations may be associated with one or more actions of the user (for example, driving, alcohol consumption, operating heavy equipment, and so forth).

Additional systems, methods, apparatuses, features, and aspects are realized through the techniques of various embodiments of the disclosure. Other embodiments and aspects of the disclosure are described in detail below and are considered a part of the claimed disclosure. Other embodiments and aspects can be understood with reference to the description and the drawings.

BRIEF DESCRIPTION OF DRAWINGS

Embodiments are illustrated by way of example and not limitation in the figures of the accompanying drawings, in which like references indicate similar elements and in which.

DETAILED DESCRIPTION

Systems and methods for detecting blood alcohol level according to a horizontal gaze nystagmus level of a user are described. In the detecting of a blood alcohol level of a user, an eye of the user may be captured as the eye attempts to follow a moving object. The captured video of the eye of the user may be stabilized. Since the eye movements in the video may interfere with the stabilization of the video, the eye area, in a plurality of frames of the video, may be detected and masked. The video may be thus separated into masked and unmasked portions. Using only the unmasked portion, the video may be stabilized and a shaking movement of a hand and/or head of the user may be detected. The shaking movement may be then applied to the mask. In such a way, a stabilized video of the eye area may be received.

The stabilized video may be analyzed to identify the pupil of the user in the masked area. Then, the velocity of the pupil may be estimated between the plurality of frames of the stabilized video, and any shifts in the velocity may be identified. The one or more shifts may be assessed to determine the horizontal gaze nystagmus level according to a lookup table. Then, a blood alcohol level equivalent to the determined horizontal gaze nystagmus level may be identified and output to the user via an interface.

Figure 1:
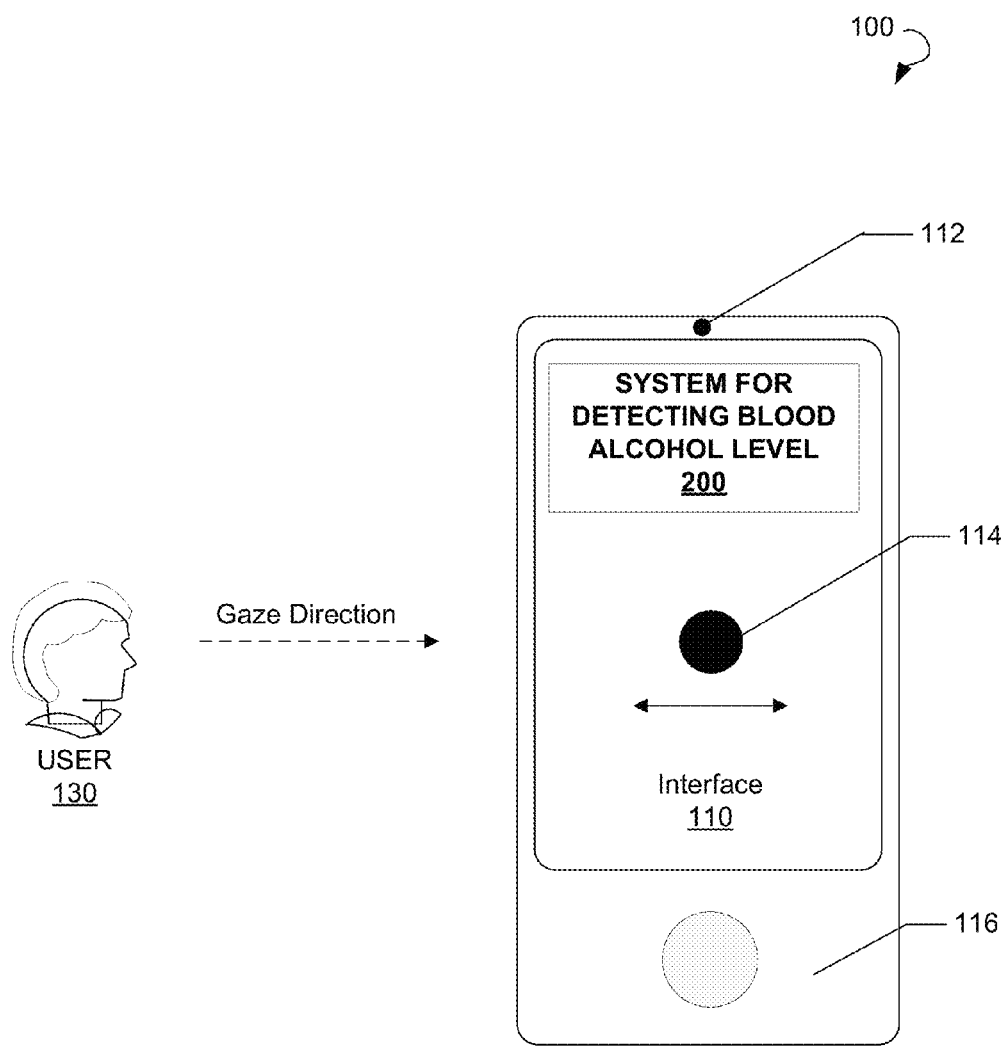
FIG. 1 illustrates an environment within which the systems and methods for detecting blood alcohol level can be implemented, in accordance to some embodiments.

Referring now to the drawings, FIG. 1 illustrates an environment 100 within which the systems and methods for detecting blood alcohol level can be implemented, in accordance to some embodiments. The environment 100 may include a user device 116 and a user 130. The user device 116 may include a mobile telephone, a smartphone, a computer, a personal digital assistant (PDA), a laptop, a tablet Personal Computer (PC), and so forth.

Conventional computing devices, such as the user device 116, provide various hardware capabilities, including a processor, a screen, a light source, a receiver, and a communications interface. Thus, in one embodiment of the present disclosure, a software application may be created, for example, an iPhone application or Android application, which configures an existing user device 116 to perform operations of a method for detecting blood alcohol level. In this embodiment, a system for detecting blood alcohol level 200 may reside on the user device 116. The user 130, in some example embodiments, may interact with the system 200 via an interface 110.

Thus, the system 200 may display a moving object 114 on a screen of the user device 116. The moving object may move from one side of the screen to the opposite side one or more times. In some example embodiments, the moving object 114 travels from one side to the opposite two times.

The user 130 may follow the moving object 114 with his eyes. Meanwhile, movements of an eye of the user may be captured by a receiver. The user 130 may be in a standing, sitting, or supine position when having a blood alcohol level detected.

In some embodiments, the user device 116 may include a light source 112. The light source 112 may be configurable to generate red light to illuminate the eye of the user when detecting blood alcohol level.

Figure 2:
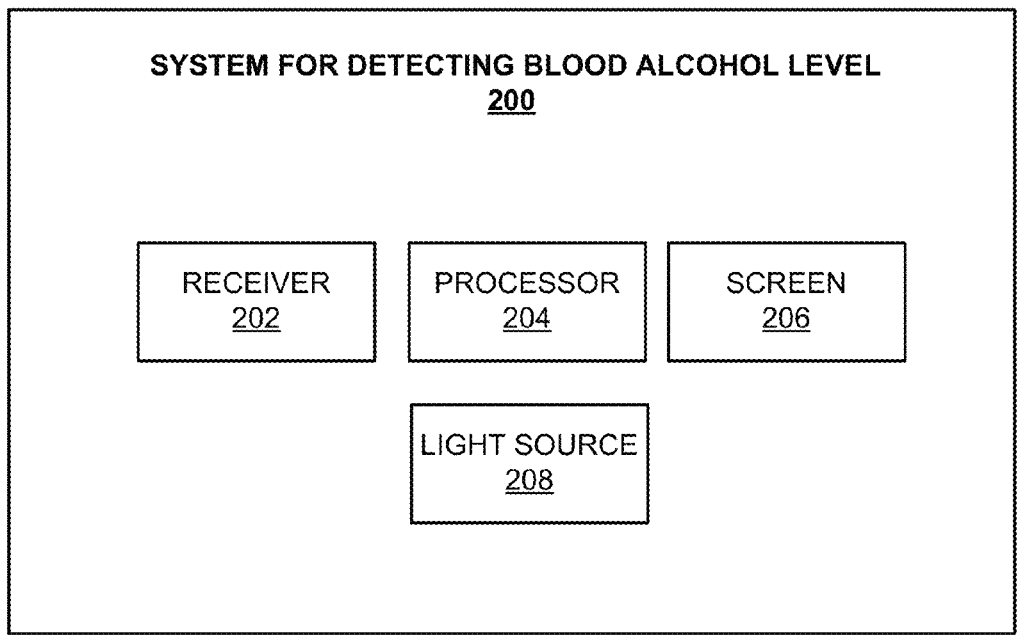
FIG. 2 illustrates an example system for detecting blood alcohol level, in accordance to some embodiments.

An example system 200 for detecting blood alcohol level is illustrated by FIG. 2. The system 200 may comprise a receiver 202, a processor 204, a screen 206, and a light source 208.

The screen 206 may include a liquid crystal display (LCD), a touch screen, and so forth, and may be configurable to display an object that moves across the screen 206. The object may move horizontally or vertically with a speed convenient for a user to follow the object with his eyes. The object moves may repeat two or more times to increase reliability of the blood alcohol level detection. The receiver 202 may be configurable to receive an input video of an eye of the user. In various embodiments, the receiver 202 may include a camera, a recording device, and so forth.

In some embodiments, the input video may be approximately 30 seconds long.

The user eye captured by the receiver 202 may be illuminated by red light. The red light may be generated by a light source 208 and/or screen 206.

The input video received by the receiver 202 may be then processed by the processor 204. As used herein, the processor 204 may include a programmable processor, such as a microcontroller, central processing unit (CPU), and so forth. In other embodiments, the processor 204 may include an application-specific integrated circuit (ASIC) or programmable logic array (PLA), such as a field programmable gate array (FPGA), designed to implement the functions performed by the system 200. Thus, the processor 204 may stabilize the input video by masking the eye area and stabilizing the unmasked portion of the video. In such a way, a shaking movement of the receiver 202 may be detected and applied to the eye area that was masked.

After that, the stabilized eye area of the input video may be analyzed to identify a pupil of the user. Once identified, the processor 204 may estimate a velocity of the pupil and identify one or more shifts in the velocity. Based on the one or more shifts, a horizontal gaze nystagmus level may be determined using a lookup table.

Based on the horizontal gaze nystagmus level, an equivalent blood alcohol level of the user may be then determined and output via the interface of the system 200 on a screen 206.

Figure 3:
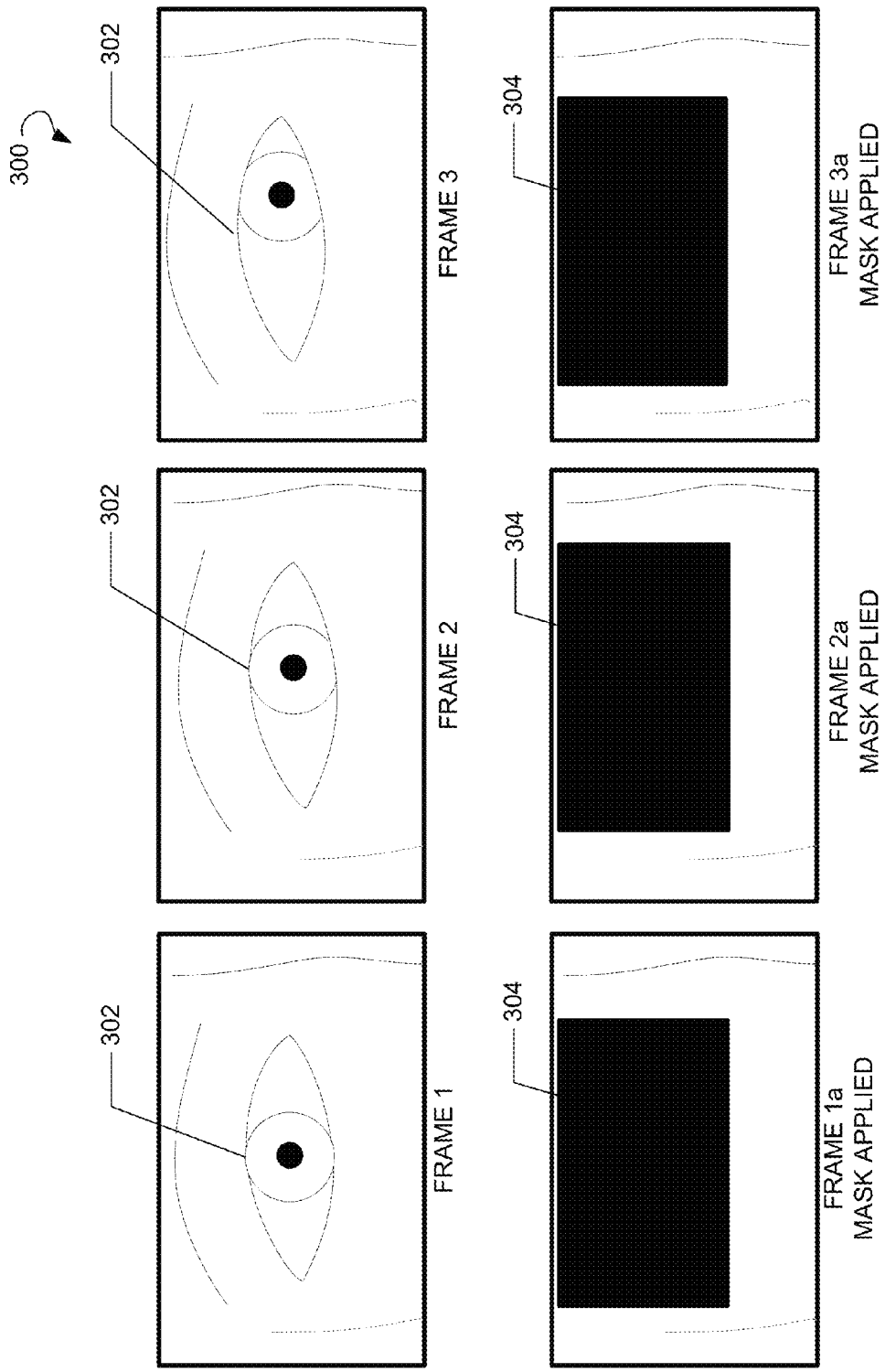
FIG. 3 illustrates an example masking of an eye area, in accordance to certain example embodiments.

Masking an eye area in the input video may be illustrated by FIG. 3. FIG. 3 shows a sequence 300 of frames of the input video, in accordance to some example embodiments. Frames 1-3 illustrate moving of an eye 302 of the user while following a moving object. An eye area may be detected at one of the frames of the input video and a mask 304 may be created to exclude the eye area for the purpose of video stabilizing. The mask 304 may be applied to all frames of the input video as shown by frames 1a-3a.

With the mask applied, the input video may be stabilized without eye movements interfering with the stabilization process. Thus, a shaking movement, including shaking of a receiver and/or head of the user, may be detected.

Figure 4:
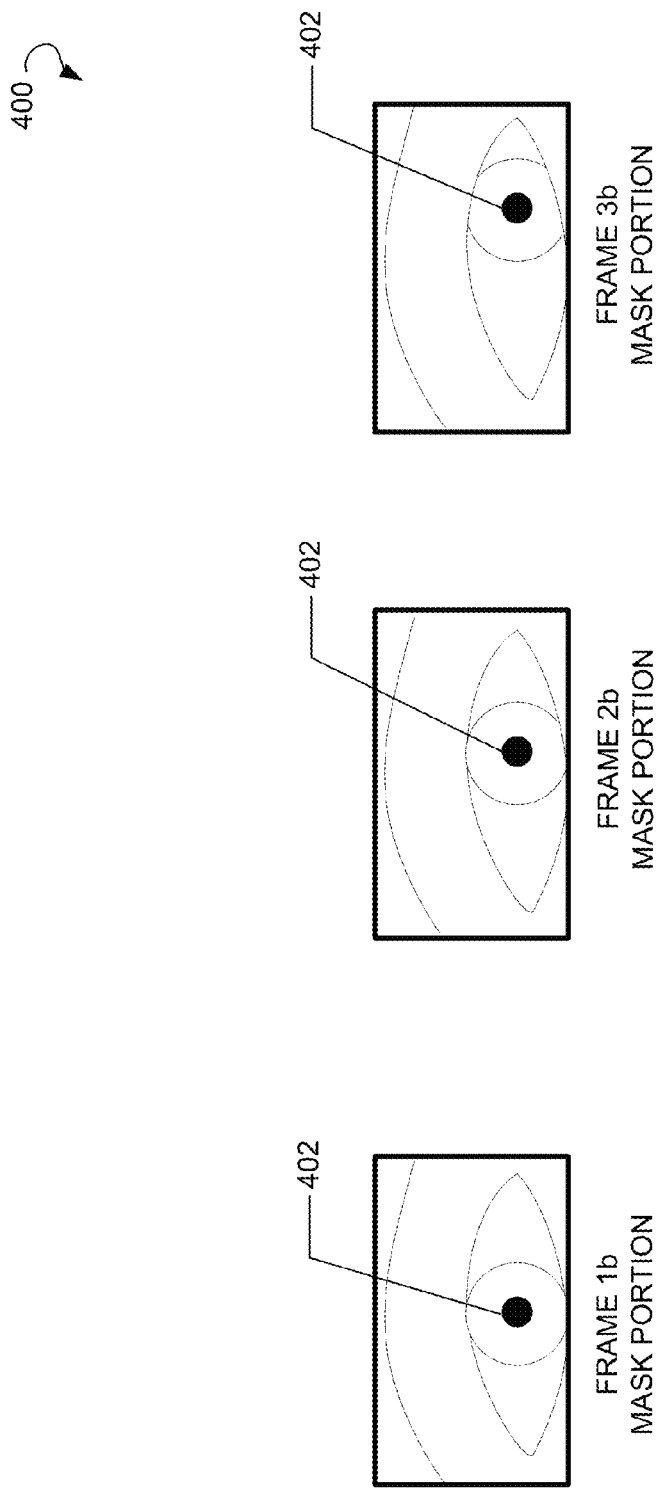
FIG. 4 illustrates an example stabilized eye area in a plurality of frames, in accordance to certain example embodiments.

The shaking movement may be applied to the masked portion to receive a video of the eye area without shaking (i.e., stabilized video). The stabilized frames 400 of the eye area (masked portion) are illustrated by FIG. 4.

Frames 1b-3b mask portion show the eye area that was masked for stabilization. The shaking movement is removed, so it may not influence further processing of the video and thus the accuracy of blood alcohol level detection.

Frames 1b-3b may be then analyzed by the system to identify a pupil 402 of the user.

In some embodiments, to identify the pupil 402 of the user, a standard deviation of each pixel in the eye area may be computed. The pixels with the largest standard deviation may be determined and dilated to find the largest connected component. Then, a shape of the connected component may be determined and a circular component chosen. The system may also consider relative size of the components to find the component composing approximately 10% of the eye area. The found component may be the pupil 402.

In an alternative embodiment, to identify the pupil 402 of the user, a Circular Hough Transformation can be applied to the image and a center and radius of the strongest circular component can be determined. The system may also consider relative size of the found circular components to find the component composing approximately 10% of the eye area. The found component may be the pupil 402.

The system may then estimate a velocity of the pupil between the plurality of frames of the input video and, based on the estimation, identify one or more shifts in the velocity. In some embodiments, the one or more shifts may be associated with a jump in brightness of a frame every 3-5 pixels.

When the one or more shifts are detected, they may be used to determine the horizontal gaze nystagmus level using a lookup table. An equivalent blood alcohol level may be determined based on the horizontal gaze nystagmus level as shown by FIG. 5.

Figure 5:
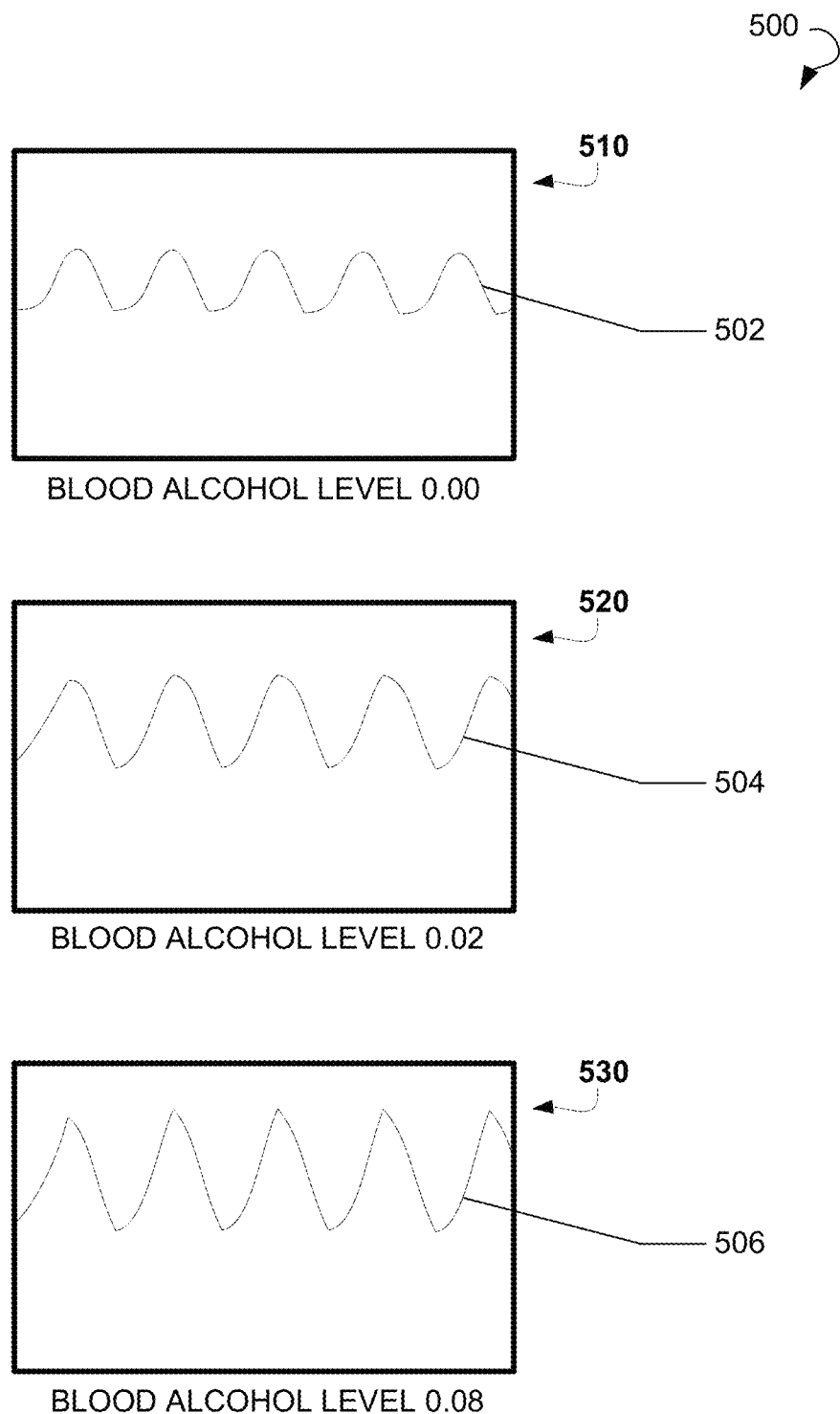
FIG. 5 illustrates example horizontal gaze nystagmus levels in relation to various blood alcohol levels, in accordance to certain example embodiments.

FIG. 5 illustrates various paths 500 of horizontal gaze nystagmus levels associated with specific blood alcohol levels. Small HGN may be present even when the user is sober. However, consuming alcohol or drugs makes horizontal gaze nystagmus more pronounced. Thus, diagram 510 shows a path 502 that represents horizontal gaze nystagmus level at zero level of blood alcohol.

Diagram 520 shows eye jerking associated with blood alcohol level (BAL) of 0.02%. A path 504 represents the eye jerking that is more pronounced in comparison to the path 502 in diagram 510. The blood alcohol level of 0.02% means 0.2% (permille) or 0.02 grams of alcohol per 100 grams of blood of a person.

Diagram 530 illustrates horizontal gaze nystagmus level associated with blood alcohol level of 0.08%. A path 506 shows a higher HGN at 0.08% BAL than at 0.02 or 0.00% BAL.

HGN will also become pronounced if the user looks more at an angle, rather than looking straight ahead. So on FIG. 5 a user with BAL of 0.02% can show a path 502 when looking at an angle of 30% to the moving dot on the display, but display a path 506 when the angle exceeds 30%.

Figure 6:
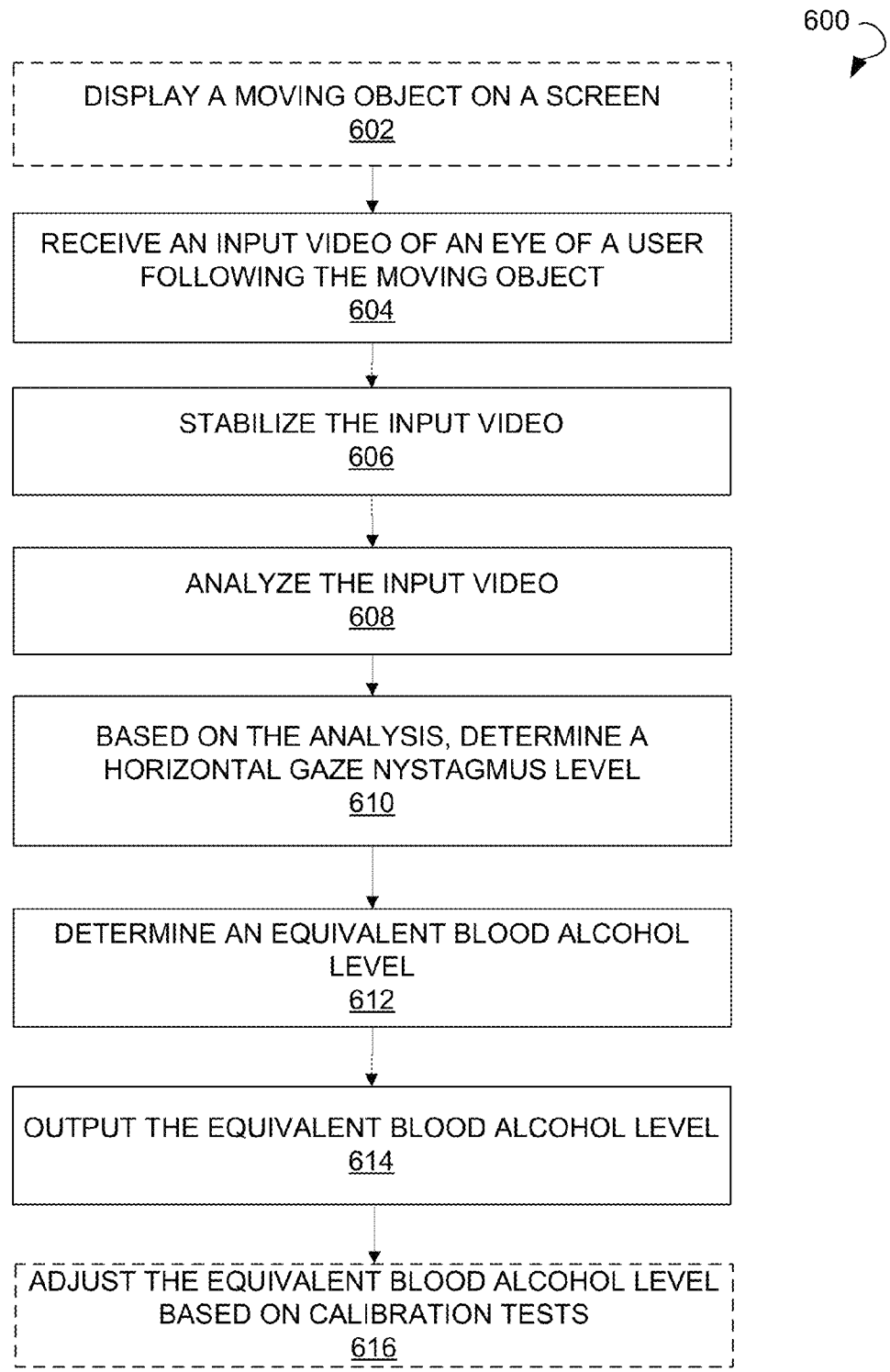
FIG. 6 is a flow chart illustrating a method for detecting blood alcohol level, in accordance with certain embodiments.

FIG. 6 is a flow chart illustrating a method 600 for detecting blood alcohol level, in accordance with certain embodiments. Method 600 may start with an optional operation 602 of displaying a moving object traveling horizontally or vertically.

In some embodiments, the moving object may move from one side of the screen to the opposite side at least twice.

An eye of a user who follows the moving object with his eyes may be captured. In some embodiments, the eye of the user may be illuminated by red light generated, for example, by the screen and/or by another light source. Thus, an input video of the eye of the user following the moving object may be received at operation 604.

The duration of the input video, according to some embodiments, may be 30 seconds.

The method 600 may proceed with stabilizing the input video by a processor at operation 606. The stabilizing may include creating a masked and unmasked portion of the input video. The masked portion may be the portion masking an eye area. The unmasked portion, comprising the rest of the video, may be used to stabilize the video. The process of stabilizing the input video is described in detail with reference to FIG. 7.

At operation 608, the input video may be analyzed to identify a pupil of the user in the mask. In some embodiments, the pupil may be identified based on a standard deviation of each pixel in the mask. The pixels with the largest standard deviation may be determined and dilated to find the largest connected component. The pupil is circular in shape, so non-circular components may be neglected. If more than one circular component is left, a relative size of the components may be determined. The component composing approximately 10% of the eye area may be identified as the pupil.

Based on the analysis, a horizontal gaze nystagmus level may be determined at operation 610. HGN may be determined using an estimated velocity of the pupil between frames of the input video. Detected shift in the velocity may be associated with HGN onset. Then, the level of the detected HGN may be determined and assessed. Detailed description of HGN level determining is presented below with reference to FIG. 8.

At operation 612, a blood alcohol level equivalent to the determined HGN level may be determined using a lookup table. The equivalent blood alcohol level may be output, for example, using the screen, at operation 614.

In some embodiments, the equivalent blood alcohol level may be adjusted based on individual calibration tests that may be optionally performed by the user. During a calibration test, the equivalent blood alcohol level of the user may be determined, and an actual blood alcohol level of the user at the moment of detection may be received from the user. The user may determine the actual blood alcohol level using conventional methods, for example, by an alcohol measure unit or estimation based on the number of drinks in relation to time. A calibration test may be repeated several times with various blood alcohol levels.

Using the data of the performed calibration tests, the equivalent blood alcohol level may be adjusted to determine the blood alcohol level more accurately considering individual characteristics of the user.

Based on the equivalent BAL or adjusted equivalent BAL, safety recommendations related to driving ability of the user may be generated. For example, the safety recommendations may include a recommendation not to drive if the detected BAL exceeds a certain value. Additionally, the safety recommendations may include a recommendation to stop consuming alcohol. In some embodiments, the user may predetermine the BAL at which he desires to stop consuming alcohol.

Figure 7:
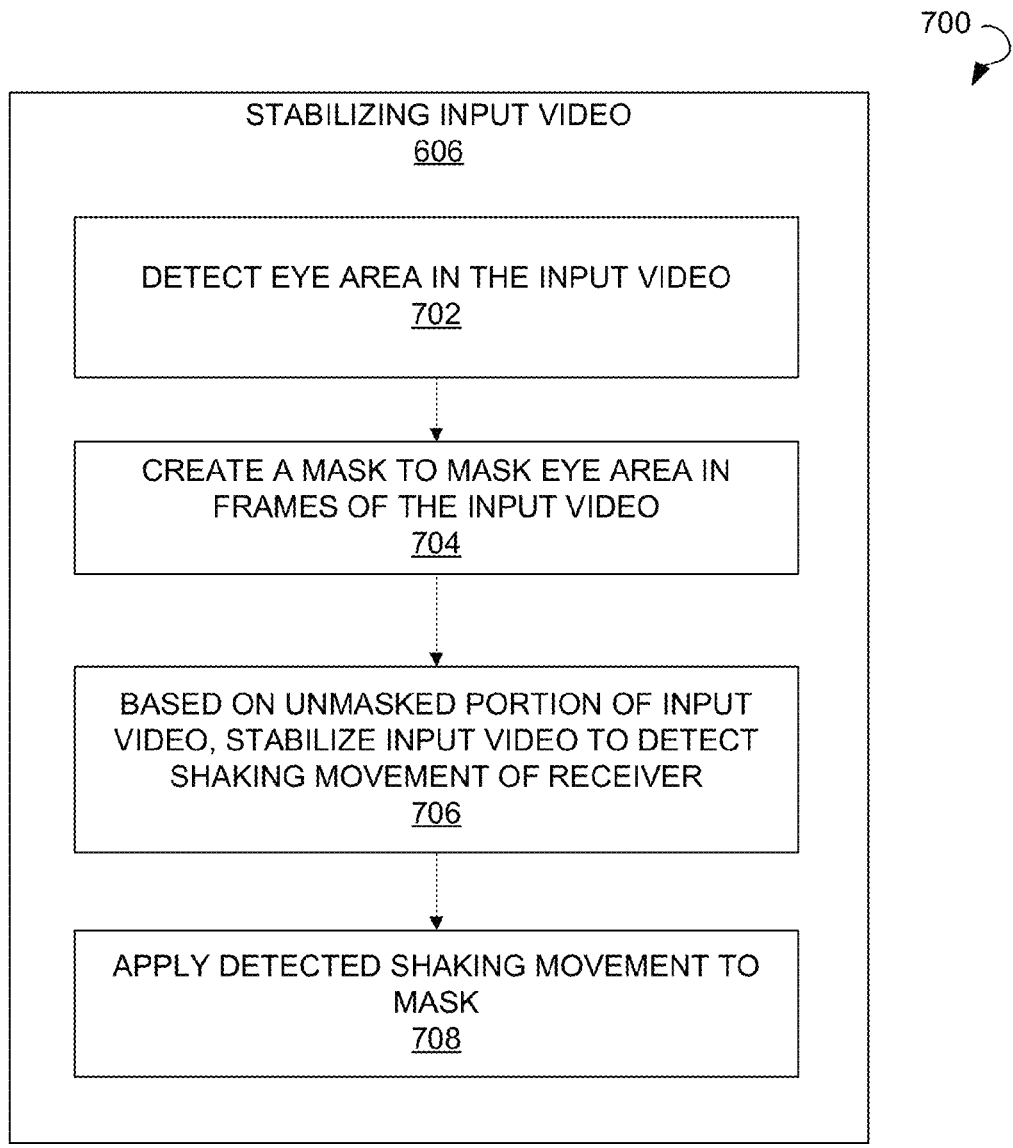
FIG. 7 is a flow chart illustrating operations included in a stabilizing of input video, in accordance with certain embodiments.

FIG. 7 illustrates a detailed sequence 700 of operations that operation 606 of method 600 may include, in accordance to some embodiments. Thus, stabilizing may commence at operation 702 with detecting an eye area in one or more first frames of the input video. For example, the eye area may be detected in the first 100 frames of the input video. In some embodiments, at operation 704, the eye area may be masked by a mask having a shape of a square. The square may be enlarged to allow for shaking of a receiver and/or head of the user and taken to all frames of the input video. Thus, the eye area may be masked on all frames of the input video so that eye movements do not interfere with stabilizing of the input video.

The mask may be referred to as a masked portion and the rest of the frame may be referred to as an unmasked portion. At operation 706, based on the unmasked portion, the input video may be stabilized to detect a shaking movement of the receiver. When the shaking movement is detected, it may be applied to the mask at operation 708.

The mask may be referred to as a masked portion and the rest of the frame may be referred to as an unmasked portion. At operation 706, based on the unmasked portion, the input video may be stabilized to detect a shaking movement of the receiver. When the shaking movement is detected, it may be applied to the mask at operation 708.

Figure 8:
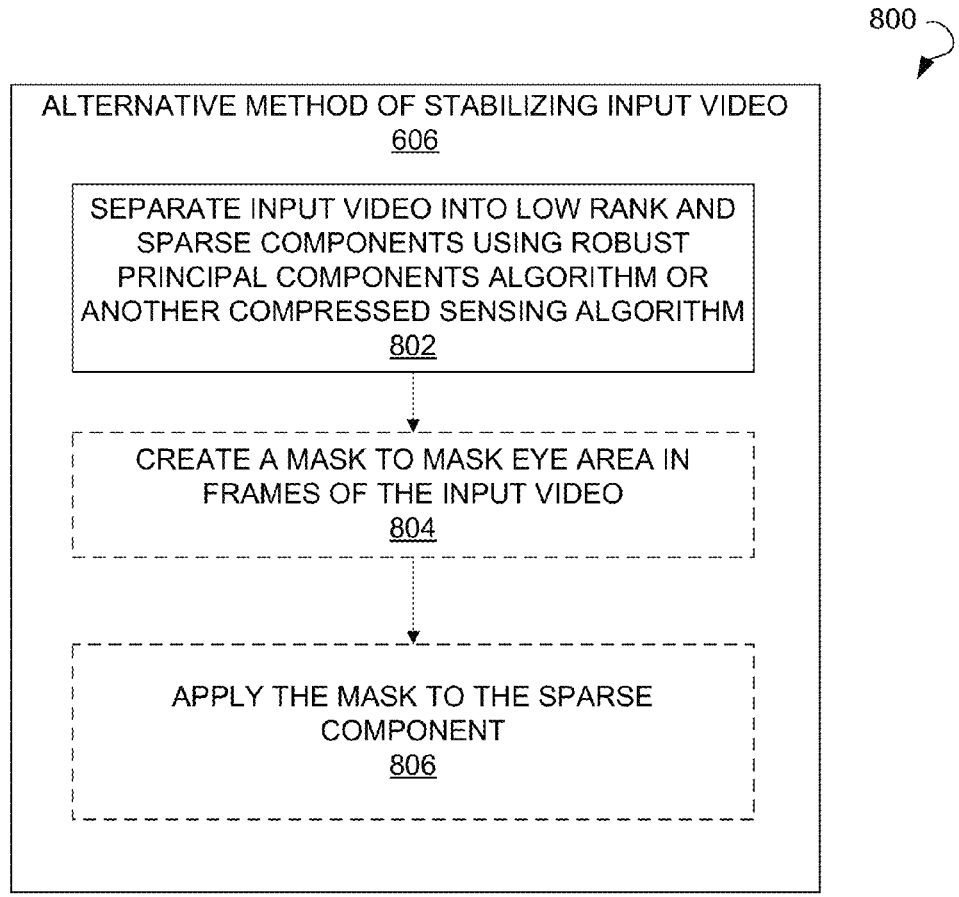
FIG. 8 is a flow chart illustrating operations included in a determining of an equivalent blood alcohol level, in accordance with certain embodiments.

FIG. 8 illustrates an alternative detailed sequence 800 of operations that operation 606 of method 600 may include, in accordance to some embodiments. Here, stabilizing may commence at operation 802 with separating the video into a low rank component and a sparse component using a compressed sensing algorithm, such as robust principal components analysis (RPCA) and its variations that estimate the camera shake together with a movement of a small area in the image, and lighting variation. In some embodiments, to estimate the RPCA, software such as TFOCS or CVX can be used. For example, the RPCA may separate a partial face and eye brows area into a low rank component and a sparse component. The low rank component may be determined based on its varying along a few principal components. The eye area into the sparse component may be determined based on the fact that the eyeball location is mostly unique on different frames.

In some embodiments, the sparse component may be used as the eye.

At optional operation 804, a further eye detection algorithm may be applied to either the original video, or the low rank component. The applied algorithm may create a mask to mask an eye area in the frames of the input video. The applied algorithm may include, for example, a Viola Jones algorithm, and may further filter the sparse component to exclude pixels outside the detected eye area. Thus, at operation 806, the created mask may be applied to the sparse component.

In some embodiments, the sparse component may further be filtered by taking a standard deviation between the frames and only looking at pixels with high variation.

Additionally, the sparse component may be filtered by dilating the pixels with high variation and then looking at large connected components. In case there are multiple connected components, the sparse component may be further filtered using an algorithm like the Circular Hough Transform to detect the connected component that is most circular and whose radius is compatible with an eyeball (approximately 10-20% of the size of the video).

Figure 9:
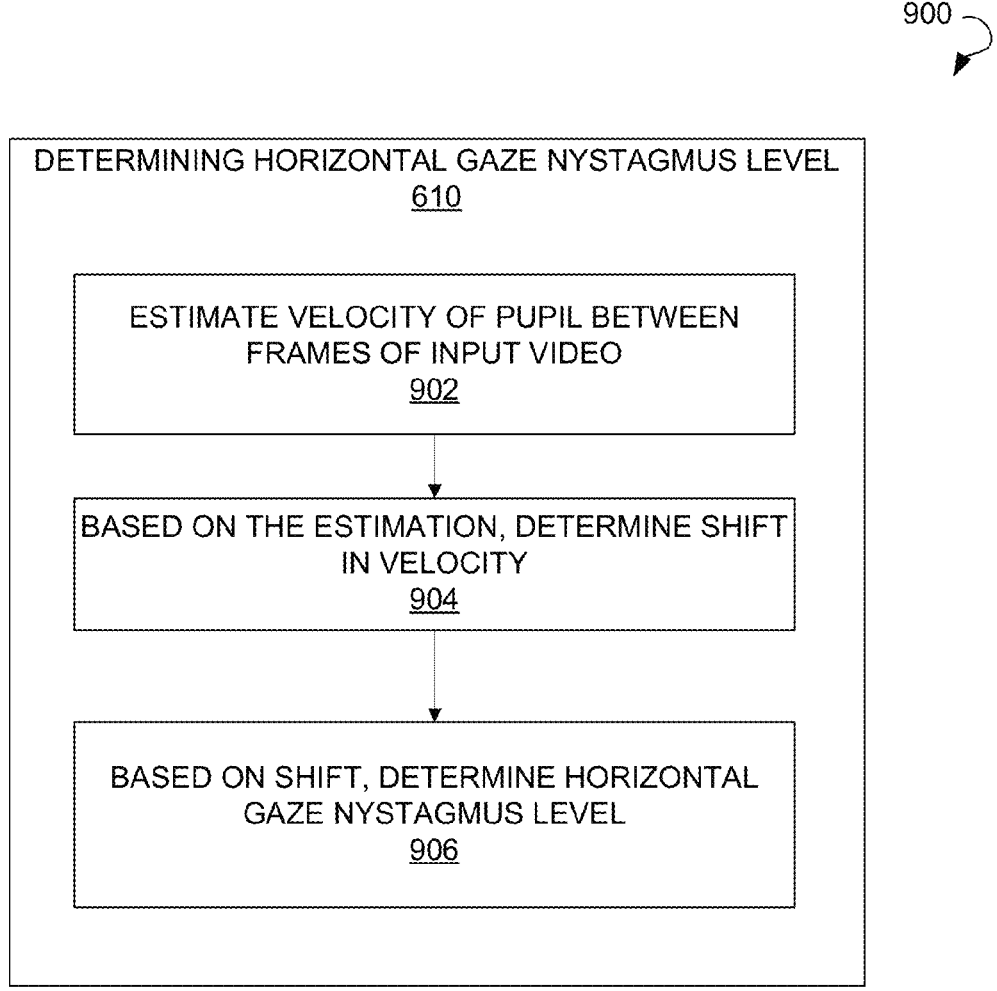
FIG. 9 is a schematic diagram illustrating an example of a computer system for performing any one or more of the methods discussed herein.

FIG. 9 illustrates a detailed sequence 900 of operations that operation 610 of method 600 may include, in accordance to some embodiments. Determining a horizontal gaze nystagmus level may be based on one or more shifts in a velocity of a pupil of the eye of the user. Thus, the determining may include estimating of a velocity of a pupil between frames of the input video at operation 902. Based on the estimation, one or more shifts in the velocity may be determined at operation 904.

In some embodiments, a shift in the velocity of the pupil may be associated with a change in brightness on the input video every 3-5 pixels.

Based on the shift, a horizontal gaze nystagmus level may be determined at operation 906. According to some embodiments, the HGN level may be determined using a lookup table.

Figure 10:
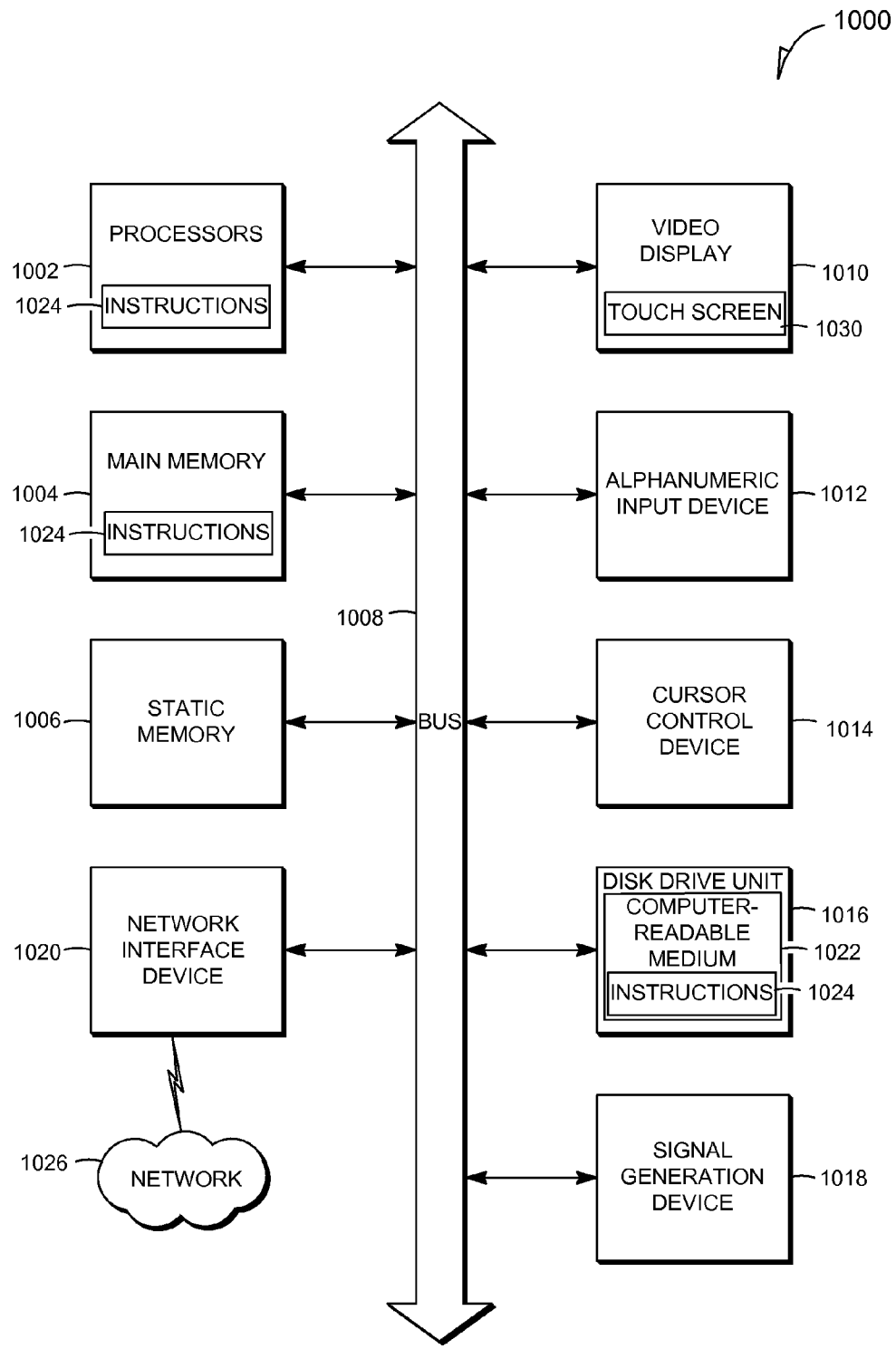
FIG. 10 is a flow chart illustrating alternative operations included in a stabilizing of input video, in accordance with certain embodiments, wherein the use of an eye mask is optional.

FIG. 10 shows a diagrammatic representation of a machine in the example electronic form of a computer system 1000, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a PC, a tablet PC, a set-top box (STB), a PDA, a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor or multiple processors 1002 (e.g., a central processing unit (CPU), a graphics processing unit (GPU), or both), a main memory 1004 and a static memory 1006, which communicate with each other via a bus 1008. The computer system 1000 may further include a video display unit 1010 (e.g., a LCD or a cathode ray tube (CRT)). The computer system 1000 may also include an alphanumeric input device 1012 (e.g., a keyboard), a cursor control device 1014 (e.g., a mouse), a disk drive unit 1016, a signal generation device 1018 (e.g., a speaker) and a network interface device 1020.

The disk drive unit 1016 includes a computer-readable medium 1022, on which is stored one or more sets of instructions and data structures (e.g., instructions 1024) embodying or utilized by any one or more of the methodologies or functions described herein. The instructions 1024 may also reside, completely or at least partially, within the main memory 1004 and/or within the processors 1002 during execution thereof by the computer system 1000. The main memory 1004 and the processors 1002 may also constitute machine-readable media.

The instructions 1024 may further be transmitted or received over a network 1026 via the network interface device 1020 utilizing any one of a number of well-known transfer protocols (e.g., Hyper Text Transfer Protocol (HTTP)).

While the computer-readable medium 1022 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like.

The example embodiments described herein may be implemented in an operating environment comprising software installed on a computer, in hardware, or in a combination of software and hardware.

Thus, various systems and methods for detecting blood alcohol level have been described. Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. A system for detecting a blood alcohol level, the system comprising:
 a receiver configurable to receive an input video of an eye of a user;
 a processor configurable to:
  stabilize the input video, the stabilizing including:
   detecting an eye area in the input video;
   creating a mask to mask the eye area in a plurality of frames of the input video, thereby separating the input video into a masked portion and an unmasked portion;
   using the unmasked portion of the input video to stabilize the input video and to detect a shaking movement of the receiver; and
   applying the shaking movement to the mask;
  analyze the input video, the analysis including identifying a pupil of the user in the mask;
  based on the analysis, detect a horizontal gaze nystagmus level, the detection including:
   estimating a velocity of the pupil between the plurality of frames of the input video;
   based on the estimation, identifying one or more shifts in the velocity; and
   based on the one or more shifts, determining the horizontal gaze nystagmus level according to a lookup table;
  based on the horizontal gaze nystagmus level, determine an equivalent blood alcohol level of the user; and
 an interface to output data associated with the equivalent blood alcohol level.

2. The system of claim 1, wherein the determining of the equivalent blood alcohol level is adjusted based on one or more calibration tests associated with the user.

3. The system of claim 1, further comprising a light source configurable to generate red light to illuminate the eye of the user.

4. The system of claim 1, wherein the input video is 30 seconds long.

5. The system of claim 1, further comprising a screen configurable to display a moving object, wherein the input video captures eye movements of the user following the moving object.

6. The system of claim 5, wherein the moving object moves from one side of the screen to the opposite side of the screen, the move being repeated at least twice.

7. The system of claim 1, further comprising generating safety recommendations regarding one or more actions of the user based on the output equivalent blood alcohol level, the one or more actions including driving, alcohol consumption, and operating heavy equipment.

8. A system for detecting a blood alcohol level, the system comprising:
 a receiver configurable to receive an input video of an eye of a user;
 a processor configurable to:
  stabilize the input video;
  analyze the input video;
  based on the analysis, detect a horizontal gaze nystagmus level;
  based on the horizontal gaze nystagmus level, determine an equivalent blood alcohol level of the user; and
 an interface to output data associated with the equivalent blood alcohol level; and
 wherein the stabilizing includes:
  using a compressed sensing algorithm and thereby separating the input video into a low-rank component and a sparse component; and
  using the sparse component as the eye area.

9. A system for detecting a blood alcohol level, the system comprising:
 a receiver configurable to receive an input video of an eye of a user;
 a processor configurable to:
  stabilize the input video;
  analyze the input video;
  based on the analysis, detect a horizontal gaze nystagmus level;
  based on the horizontal gaze nystagmus level, determine an equivalent blood alcohol level of the user; and
 an interface to output data associated with the equivalent blood alcohol level; and
 wherein the stabilizing includes:
  detecting an eye area in the input video;
  using a compressed sensing algorithm and thereby separating the input video into a low-rank component and a sparse component;
  creating a mask to mask area outside the eye area in a plurality of frames of the sparse component video; and
  using the masked sparse component as the eye area.

10. A method for detecting a blood alcohol level, the method comprising:
 receiving an input video of an eye of a user;
 detecting an eye area in the input video;
 creating a mask to mask the eye area in a plurality of frames of the input video, thereby creating a masked portion and an unmasked portion;
 stabilizing the input video based on the unmasked portion of the input video, thereby detecting a shaking movement of the receiver; and
 applying the shaking movement to the mask;
 identifying a pupil of the user in the mask;
 based on the identification, estimating a velocity of the pupil between the plurality of frames of the input video;
 based on the estimation, identifying one or more shifts in the velocity;
 based on the one or more shifts, determining the horizontal gaze nystagmus level;
 based on the horizontal gaze nystagmus level, determining an equivalent blood alcohol level of the user; and
 outputting the equivalent blood alcohol level to a screen.

11. The method of claim 10, further comprising adjusting the equivalent blood alcohol level based on one or more calibration tests associated with the user.

12. The method of claim 10, wherein the input video is captured in a red light provided by a light source.

13. The method of claim 10, further comprising displaying, on the screen, a moving object, wherein the input video captures eye movements of the user following the moving object.

14. The method of claim 13, wherein the moving object moves from one side of the screen to the opposite side of the screen, the move being repeated at least twice.

15. The method of claim 10, further comprising providing, based on the output equivalent blood alcohol level, safety recommendations associated with one or more actions of the user, the one or more actions including driving, alcohol consumption, and operating heavy equipment.

16. A method for detecting a blood alcohol level, the method comprising:
 receiving an input video of an eye of a user;

stabilizing the input video;
analyzing the input video;
based on the analysis, detecting a horizontal gaze nystagmus level;
based on the horizontal gaze nystagmus level, determining an equivalent blood alcohol level of the user;
outputting the equivalent blood alcohol level to a screen; and wherein the stabilizing includes:
separating the input video into a low rank component and a sparse component using a compressed sensing algorithm; and
using the sparse component as the eye.

17. The method of claim 16, wherein the analysis includes identifying a pupil of the user in the mask.

18. The method of claim 17, wherein the detection of the horizontal gaze nystagmus level includes:
estimating a velocity of the pupil between the plurality of frames of the input video;
based on the estimation, identifying one or more shifts in the velocity; and
based on the one or more shifts, determining the horizontal gaze nystagmus level.

19. A non-transitory machine-readable medium comprising instructions that, when executed, perform the following operations:
display, on a screen, a moving object;
receive an input video of an eye of a user, wherein the input video captures the eye of the user following the moving object;
detect an eye area in the input video;
create a mask to mask the eye area in a plurality of frames of the input video, thereby creating an unmasked portion and a masked portion of the input video;
based on the unmasked portion of the input video, stabilize the input video to detect a shaking movement of the receiver;
apply the shaking movement to the mask;
identify a pupil of the user in the mask;
based on the identification, estimate a velocity of the pupil between the plurality of frames of the input video;
based on the estimation, identify one or more shifts in the velocity;
determine a horizontal gaze nystagmus level associated with the one or more shifts in a lookup table;
based on the horizontal gaze nystagmus level, detect an equivalent blood alcohol level; and
output the equivalent blood alcohol level to the screen.

20. A non-transitory machine-readable medium comprising instructions that, when executed, perform the following operations:
display, on a screen, a moving object;
receive an input video of an eye of a user, wherein the input video captures the eye of the user following the moving object;
detect an eye area in the input video;
separate the video into a low rank component and a sparse component;
erase pixels outside the detected eye area from the sparse component to generate a masked sparse component;
identify a pupil of the user in the masked sparse component;
based on the identification, estimate a velocity of the pupil between the plurality of frames of the input video;
based on the estimation, identify one or more shifts in the velocity;
determine a horizontal gaze nystagmus level associated with the one or more shifts in a lookup table;
based on the horizontal gaze nystagmus level, detect an equivalent blood alcohol level; and
output the equivalent blood alcohol level to the screen.

* * * * *